(12) United States Patent
Mullaney

(10) Patent No.: US 9,149,296 B2
(45) Date of Patent: Oct. 6, 2015

(54) CAM DRIVEN JAW FOR EXTERNAL FIXATION CLAMPS

(75) Inventor: Michael W. Mullaney, Kinnelon, NJ (US)

(73) Assignee: Zimmer, Inc., Warsaw, IN (US)

(*) Notice: Subject to any disclaimer, the term of this patent is extended or adjusted under 35 U.S.C. 154(b) by 688 days.

(21) Appl. No.: 13/315,535

(22) Filed: Dec. 9, 2011

(65) Prior Publication Data

US 2012/0150184 A1 Jun. 14, 2012

Related U.S. Application Data

(60) Provisional application No. 61/421,492, filed on Dec. 9, 2010.

(51) Int. Cl.
A61B 17/64 (2006.01)

(52) U.S. Cl.
CPC .................. *A61B 17/6466* (2013.01)

(58) Field of Classification Search
CPC ... A61B 17/6466; A61B 17/645; A61B 17/60
USPC .............. 403/385, 389, 396, 321, 322.1, 325; 606/54, 59
See application file for complete search history.

(56) References Cited

U.S. PATENT DOCUMENTS

| | | |
|---|---|---|
| 1,706,215 A | 3/1929 | Davidson |
| 2,705,603 A | 4/1955 | Bitz et al. |
| 3,044,512 A | 7/1962 | Jones |
| 3,154,331 A | 10/1964 | Engelhardt |
| 3,373,465 A * | 3/1968 | Johnson et al. ................. 24/490 |
| 3,406,987 A | 10/1968 | Hunder et al. |
| 4,037,978 A | 7/1977 | Connelly |
| 4,115,966 A | 9/1978 | DeLee |
| 4,312,488 A | 1/1982 | Pierron |
| 4,388,747 A | 6/1983 | Plummer |
| 4,483,334 A | 11/1984 | Murray |

(Continued)

FOREIGN PATENT DOCUMENTS

| | | |
|---|---|---|
| DE | 2430234 | 1/1975 |
| EP | 1820461 | 8/2007 |

(Continued)

OTHER PUBLICATIONS

Swiss Patent Office, Application No. 03 891/90-6, titled "Fixateur externe," Applicant—Jaquet Orthopedie S.A., filed Dec. 16, 1991, 34 pages.

(Continued)

*Primary Examiner* — Daniel Wiley
(74) *Attorney, Agent, or Firm* — Schwegman Lundberg & Woessner, P.A.

(57) ABSTRACT

A clamp includes an opening structurally arranged to receive a fixation element with a cam driven jaw. The clamping assembly includes a first jaw and a second jaw disposed relative to the first jaw. The first and second jaws may be cooperatively positioned to receive the fixation element. A sliding cam is configured to displace relative the first and second jaws. The sliding cam may be associated with the first and second jaws to force the first jaw to vertically displace relative to the second jaw. In one aspect, the sliding cam is structured to vertically displace the first jaw enough to permit an external fixation element to be received between the first and second jaws.

27 Claims, 10 Drawing Sheets

(56) References Cited

U.S. PATENT DOCUMENTS

| | | | |
|---|---|---|---|
| 4,620,533 A | 11/1986 | Mears | |
| 4,653,481 A | 3/1987 | Howland et al. | |
| 4,662,365 A | 5/1987 | Gotzen et al. | |
| 4,700,437 A | 10/1987 | Hoshino | |
| D295,725 S | 5/1988 | Shioda | |
| 4,817,897 A | 4/1989 | Kreusel | |
| 5,312,405 A | 5/1994 | Korotko et al. | |
| 5,427,465 A | 6/1995 | Sato | |
| 5,662,648 A | 9/1997 | Faccioli et al. | |
| 5,683,389 A | 11/1997 | Orsak | |
| 5,709,681 A | 1/1998 | Pennig | |
| 5,727,899 A | 3/1998 | Dobrovolny | |
| 5,741,252 A | 4/1998 | Mazzio et al. | |
| 5,746,741 A | 5/1998 | Kraus et al. | |
| 5,752,954 A | 5/1998 | Mata et al. | |
| 5,800,548 A | 9/1998 | Martin et al. | |
| 5,827,282 A | 10/1998 | Pennig | |
| 5,860,728 A | 1/1999 | Maglica | |
| 5,891,144 A | 4/1999 | Mata et al. | |
| 5,976,141 A | 11/1999 | Haag et al. | |
| 6,022,348 A | 2/2000 | Spitzer | |
| 6,080,153 A | 6/2000 | Mata et al. | |
| 6,102,911 A | 8/2000 | Faccioli et al. | |
| 6,217,577 B1 | 4/2001 | Hofmann | |
| 6,277,069 B1 | 8/2001 | Gray | |
| 6,376,775 B1 | 4/2002 | Leijon et al. | |
| 6,386,786 B1 | 5/2002 | Perlman et al. | |
| 6,409,729 B1 | 6/2002 | Martinelli | |
| 6,500,177 B1 | 12/2002 | Martinelli et al. | |
| 6,637,082 B1 | 10/2003 | Chang | |
| 6,652,523 B1 | 11/2003 | Evrard et al. | |
| 6,702,814 B2 | 3/2004 | Walulik et al. | |
| 6,716,212 B1 | 4/2004 | Pickens | |
| 6,736,775 B2 | 5/2004 | Phillips | |
| 6,887,197 B2 | 5/2005 | Phillips | |
| 7,004,943 B2 | 2/2006 | Ferrante et al. | |
| 7,048,735 B2 | 5/2006 | Ferrante et al. | |
| 7,097,616 B2 * | 8/2006 | Bjork et al. | 600/230 |
| 7,241,071 B2 | 7/2007 | Carraher et al. | |
| 7,241,074 B2 | 7/2007 | Thomket et al. | |
| 7,261,713 B2 | 8/2007 | Langmaid | |
| 7,314,331 B1 | 1/2008 | Koros et al. | |
| 7,320,556 B2 | 1/2008 | Vagn-Erik | |
| 7,473,223 B2 | 1/2009 | Fetzer | |
| 7,491,008 B2 | 2/2009 | Thomke et al. | |
| 7,527,626 B2 | 5/2009 | Lutz et al. | |
| 7,562,855 B2 | 7/2009 | Oetlinger | |
| 7,588,537 B2 | 9/2009 | Bass | |
| 7,708,736 B2 | 5/2010 | Mullaney | |
| 7,744,632 B2 | 6/2010 | Usher | |
| 7,887,537 B2 * | 2/2011 | Ferrante et al. | 606/59 |
| 7,938,829 B2 * | 5/2011 | Mullaney | 606/59 |
| 2001/0004432 A1 | 6/2001 | Pfister | |
| 2002/0037193 A1 | 3/2002 | Gibbons et al. | |
| 2002/0042613 A1 | 4/2002 | Mata | |
| 2002/0061225 A1 | 5/2002 | Boucher et al. | |
| 2002/0165543 A1 | 11/2002 | Winquist et al. | |
| 2003/0149429 A1 | 8/2003 | Ferranet et al. | |
| 2003/0191370 A1 * | 10/2003 | Phillips | 600/201 |
| 2004/0044344 A1 * | 3/2004 | Winquist et al. | 606/54 |
| 2005/0113831 A1 | 5/2005 | Franck et al. | |
| 2005/0119656 A1 * | 6/2005 | Ferrante et al. | 606/59 |
| 2006/0017566 A1 | 1/2006 | Gauvreau et al. | |
| 2006/0039750 A1 | 2/2006 | Thomke | |
| 2006/0229602 A1 | 10/2006 | Olsen | |
| 2006/0229603 A1 | 10/2006 | Olsen | |
| 2006/0255521 A1 | 11/2006 | Brunner | |
| 2006/0271045 A1 | 11/2006 | Hubbard et al. | |
| 2006/0287652 A1 | 12/2006 | Lessig et al. | |
| 2007/0038217 A1 | 2/2007 | Brown et al. | |
| 2007/0049932 A1 | 3/2007 | Richelsoph et al. | |
| 2007/0198012 A1 | 8/2007 | Thomke et al. | |
| 2007/0293860 A1 | 12/2007 | Oesch | |
| 2008/0065068 A1 | 3/2008 | Thomket et al. | |
| 2008/0215053 A1 | 9/2008 | Thomke et al. | |
| 2009/0036891 A1 | 2/2009 | Brown et al. | |
| 2009/0088751 A1 * | 4/2009 | Mullaney | 606/59 |
| 2009/0299368 A1 | 12/2009 | Bauer | |
| 2011/0098706 A1 | 4/2011 | Mullaney | |
| 2011/0098707 A1 | 4/2011 | Mullaney | |
| 2011/0172663 A1 | 7/2011 | Mullaney | |
| 2012/0004659 A1 | 1/2012 | Miller et al. | |
| 2012/0089142 A1 | 4/2012 | Mullaney et al. | |
| 2012/0095462 A1 | 4/2012 | Miller | |

FOREIGN PATENT DOCUMENTS

| | | |
|---|---|---|
| EP | 2294994 | 3/2011 |
| WO | WO-89/05126 | 6/1989 |
| WO | WO-90/11055 | 10/1990 |
| WO | WO-92/12683 | 8/1992 |
| WO | WO-98/51227 | 11/1998 |
| WO | WO-99/25264 | 5/1999 |
| WO | WO-03065911 | 8/2003 |
| WO | WO-2009/004347 | 1/2009 |
| WO | WO-2012078893 | 6/2012 |

OTHER PUBLICATIONS

European Patent Office, International Search Report and Written Opinion dated Oct. 13, 2011, Application No. PCT/US2011/042813, 11 pages.

PCT/ISA-US Office, International Search Report and Written Opinion dated Dec. 2, 2008, Application No. PCT/US08/77800, 11 pages.

"International Application Serial No. PCT/US2011/063976, International Preliminary Report on Patentability mailed Jun. 20, 2013", 5 pgs.

"International Application Serial No. PCT/US2011/063976, International Search Report mailed Apr. 10, 2012", 3 pgs.

"International Application Serial No. PCT/US2011/063976, Written Opinion mailed Apr. 10, 2012", 3 pgs.

European Patent Office, International Search Report and Written Opinion mailed Mar. 28, 2012, Application No. PCT/US2011/963985, 10 pages.

European Patent Office, International Search Report and Written Opinion mailed Mar. 20, 2012, Application No. PCT/US2011/059303, 13 pages.

European Patent Office, International Search Report and Written Opinion mailed Jan. 9, 2012, Application No. PCT/US2011/055907, 9 pages.

European Patent Office, International Search Report and Written Opinion mailed Apr. 10, 2012, Application No. PCT/US2011/063976, 8 pages.

* cited by examiner ial Patent
CAM DRIVEN JAW FOR EXTERNAL FIXATION CLAMPS

PRIORITY

This application claims priority to U.S. Provisional Patent Application 61/421,492, filed Dec. 9, 2010, incorporated herein by reference.

FIELD OF THE INVENTION

This disclosure is directed to an external fixation system, and more particularly, this disclosure is directed to an external fixation assembly having a clamp with a cam element associated with a jaw of the clamp.

BACKGROUND

External fixation systems are used to stabilize fractured bones or secure bones after corrective surgery. They are usually made up of structural members held together by clamps, all assembled by the surgeon during surgery. The clamps are placed on bone pins and are attached to bars, creating a frame to hold the bones in particular relationships. Typically, the external fixation frame is assembled in the configuration the surgeon desires, then the fracture is reduced and the clamps are tightened. Some conventional clamps have to be tightened partially to provisionally lock the bone pin or bar into the clamp. Others require insertion of a fixation element against a spring force possibly making insertion more difficult than necessary.

The present disclosure overcomes one or more of the deficiencies in the prior art.

SUMMARY

In one exemplary aspect, the present disclosure is directed to a clamping assembly configured to secure a fixation element of an external fixation assembly. The clamping assembly includes a first jaw and a second jaw disposed relative to the first jaw. The first and second jaws may be cooperatively positioned to receive the fixation element. A sliding cam is configured to displace relative the first and second jaws. The sliding cam may be associated with the first and second jaws to force the first jaw to vertically displace relative to the second jaw.

In one aspect, the sliding cam is structured to vertically displace the first jaw enough to permit an external fixation element to be received between the first and second jaws. In another aspect, a blocking element is selectively disposed between the first and second jaws to mechanically prevent displacement of the first jaw relative to the second jaw. In another aspect, the sliding cam includes a guide cam slot that comprises an irregular surface having a flat surface portion and a curved surface portion.

In another exemplary aspect, the present disclosure is directed to a clamping assembly configured to secure a fixation element of an external fixation assembly. The clamping assembly includes a first jaw and a second jaw disposed relative to the first jaw. The first and second jaws may be cooperatively positioned to receive the fixation element. A sliding cam may be associated with the inner jaw. The sliding cam may have a guide cam slot cooperatively engaged with the first jaw in a manner forcing the first jaw from a first position where the clamping assembly cannot receive a fixation element to a second position where the clamping assembly can receive a fixation element.

In one aspect, the clamping assembly comprises a latch selectively disposed between the first and second jaws. The latch is configured to physically limit the range the first jaw can travel relative to the second jaw to secure the first and second jaws in a clamping condition. In another aspect, the guide cam slot includes an arcuate portion and a linear portion.

In another exemplary aspect, the present disclosure is directed to a method of clamping a fixation element within a clamp of an external fixation system. The method may include introducing a fixation element between first and second jaws of the clamp, and manually displacing the first jaw relative to the second jaw with the fixation element. It may also include guiding the displacement of the first jaw relative to the second jaw with a guide cam associated with the first jaw and the second jaw to close the clamp and capture the fixation element.

In another exemplary embodiment, the present disclosure is directed to a method of clamping a fixation element within a clamp of an external fixation system, including introducing a fixation element in a lateral direction to an open side of an external fixation clamp, and capturing the fixation element by transforming the clamp from an open condition to a provisionally locked condition under loading applied by displacing the fixation element generally in the lateral direction and with a complete absence of any spring biasing force in a longitudinal direction to close the clamp and capture the fixation element.

In another exemplary embodiment, the present disclosure is directed to a clamping assembly configured to secure a fixation element of an external fixation assembly. The clamping assembly includes a clamp comprising a first jaw and a second jaw moveable between an open condition arranged to receive a fixation element and a provisionally locked condition arranged to capture the fixation element. The clamping assembly also includes a mechanical system structurally arranged to capture the fixation element by transforming the clamp from the open condition to the provisionally locked condition under loading applied by the fixation element generally in the lateral direction and with a complete absence of any spring biasing force in a longitudinal direction.

In one aspect, guiding the displacement comprises advancing a protrusion of the first jaw along a curved portion of the guide cam.

BRIEF DESCRIPTION OF THE DRAWINGS

Aspects of the present disclosure are best understood from the following detailed description when read with the accompanying figures.

DETAILED DESCRIPTION

Figure 1:
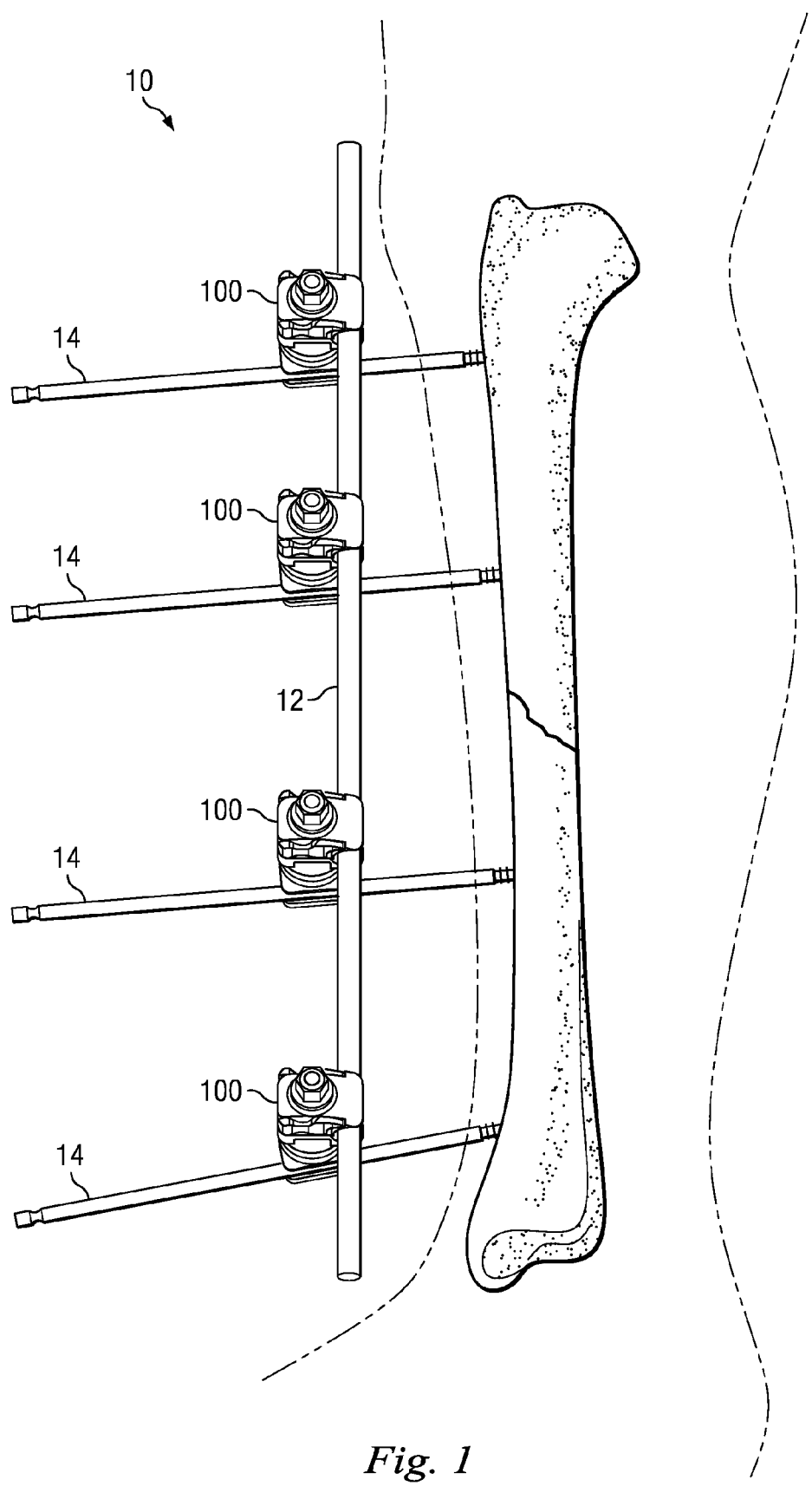
FIG. 1 is an illustration of an exemplary external fixation system in accordance with one exemplary aspect of the present disclosure connected to a patient's bone tissue.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The present disclosure is directed to an external fixation system with a clamping assembly that employs a cam mechanism that opens a clamp of the clamping assembly to permit a health care provider to introduce a fixation element, such as a fixation rod or bar (or other fixation elements) and/or pin (or other fixation elements), between opposing jaws and into the clamp. The cam mechanism then closes the clamp to capture the fixation element in a manner that prevents its removal from the clamp, unless cam sliders are actuated. Once captured, the fixation element is provisionally held in the clamp in a manner allowing the clamp to be axially displaced or slid along the fixation element or rotated about the fixation element, while preventing removal of the fixation element. Using a locking system, the clamp can be fixed in place along the fixation element to prevent movement relative to the fixation element.

In one aspect, the external fixation system includes a plurality of clamps arranged to receive and secure fixation elements that extend into or support patient tissue. These multiple clamps are arranged to pivot relative to each other about an axis coincident with a longitudinally extending post, and in some embodiments are also arranged to swivel relative to each other about an axis coincident with a transverse axle. This increases simplicity and efficiency of fixation system setup.

FIG. 1 shows an exemplary external fixation system 10 attached to a patient's fractured tibia. The system 10 includes fixation elements as rigid bars 12 and pins 14 drilled into the bone on opposing sides of the fracture. Although this disclosure references bars and pins, it should be understood that any fixation element may be used, including bone pins, wires, rings, struts, bars, rods, or other structural members. In the example in FIG. 1, each pin 14 is received into one of the clamping devices 100 by inserting the pin 14 between facing jaws of a pin clamp of the clamping device 100. Likewise, the bar 12 is received into each of the clamping devices 100 by inserting the bar 12 between facing jaws of a bar clamp of each clamping device 100 as is described further below, to establish the external fixation framework for bone stabilization. In some embodiments, inserting the bar 12 or pin 14 places the clamp in a provisionally locked condition. In this position, the respective clamp can be rotated about the bar 12 or pin 14 and may be axially displaced along the bar 12 or pin 14. In addition, at least one of the clamps may rotate about a longitudinal axis of the clamping device 100, and may pitch up or down around the cylindrical axis of a saddle element, while the jaws maintain the bar or pin in the clamp. As remaining pins 14 are connected to the bar 12 using one of the clamping devices 100, the clamping devices may be adjusted to provide angulation and orientation necessary to align the bone for healing. Additional bar-to-bar fixation clamps and/or bar-to-pin fixation clamps may be added to expand and connect the frame as required. Some embodiments include multipin clamps. Once properly created, the frame may be locked by changing the clamp from a provisionally locked condition to the locked condition.

Figure 2:
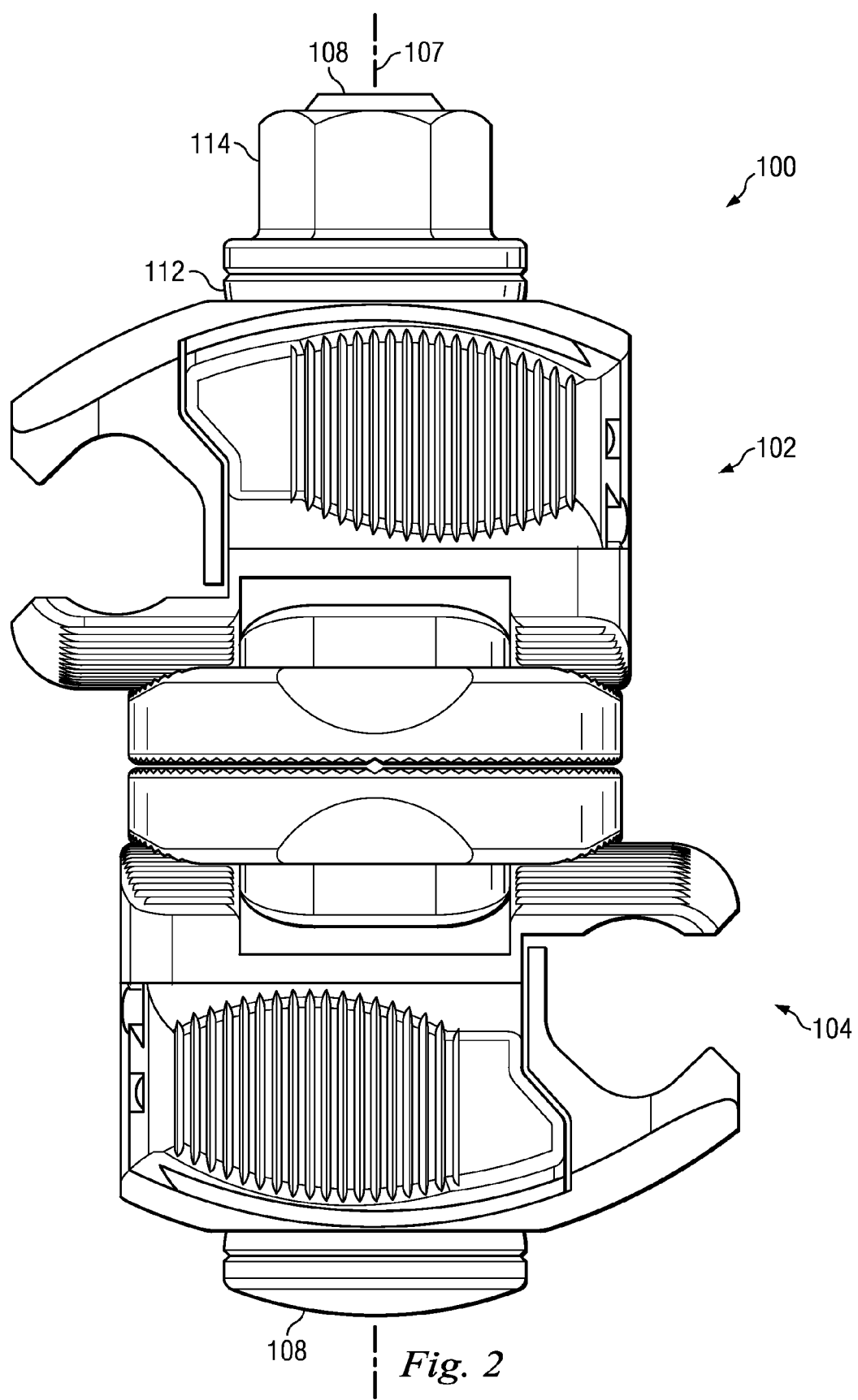
FIG. 2 is an illustration of a clamping assembly of an external fixation system according to one exemplary aspect of the present disclosure.
Figure 3:
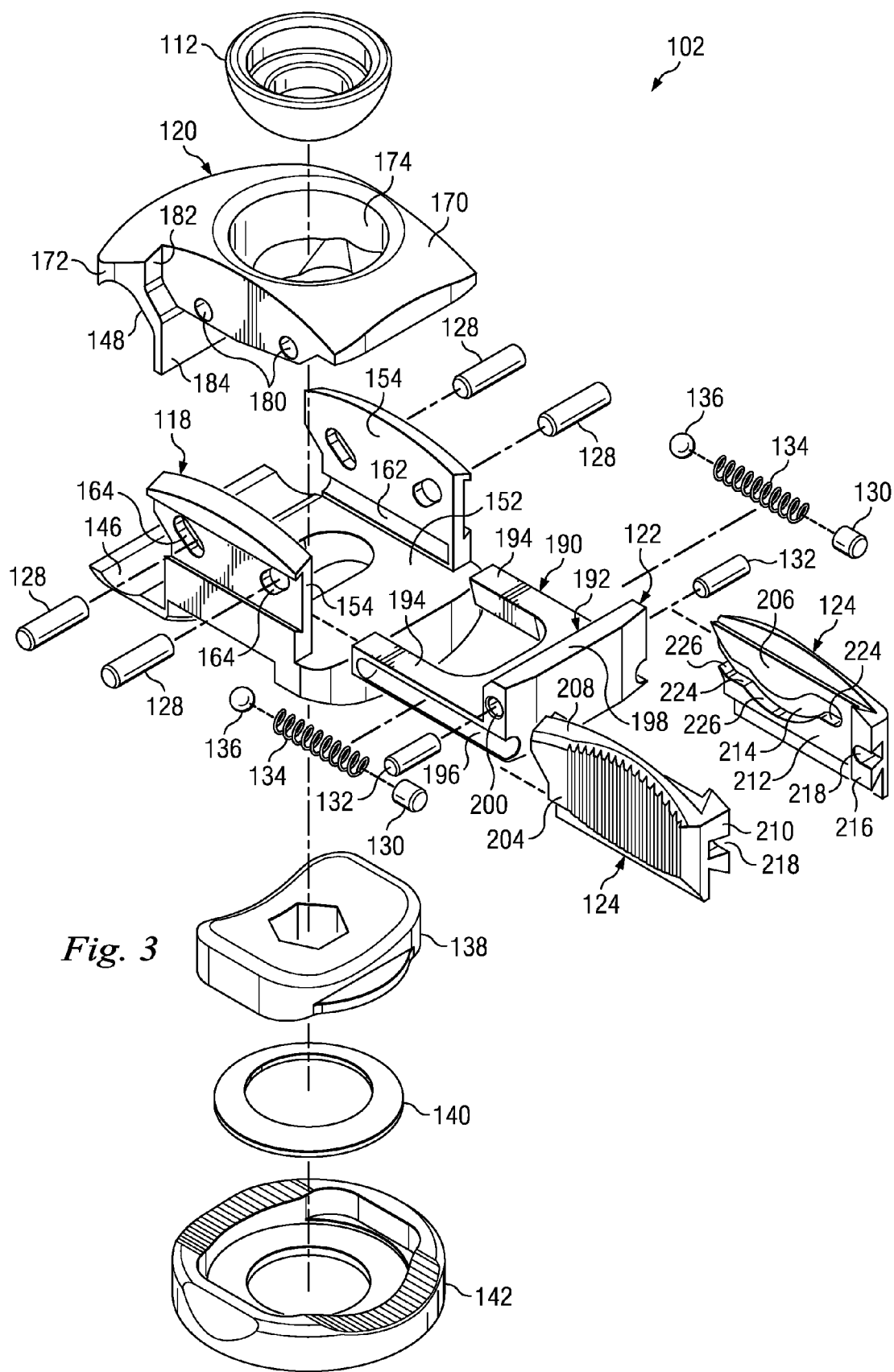
FIG. 3 is an illustration of a clamp of the clamping assembly of FIG. 2 in an exploded view.

FIGS. 2-9 show an embodiment of the clamping device 100. FIG. 2 shows a side view of the clamping device and FIG. 3 shows an exploded view of the clamping device.

FIG. 2 illustrates an exemplary clamping assembly 100 according to one exemplary aspect of the present disclosure. The clamping assembly 100 includes a clamp 102 and an essentially identical clamp 104 that are structurally configured and arranged to clamp fixation elements. In this embodiment, the clamps 102 and 104 are essentially identical constructs conceptually and both may be considered bar clamps. However other clamping assemblies may employ pin clamps with the only significant differences involving dimensional changes to accommodate different fixation element diameters if required. In other embodiments, only one of the clamps may be used with alternative types of clamping constructs, including conventional single pin or bar clamping constructs, multi-bar or pin constructs, and other clamping systems. For example, in FIG. 1, the clamping assembly 100 may be formed of a first clamp dimensionally configured to capture and secure a fixation rod while the second clamp is dimensionally configured to capture and secure a bone pin. Each clamp 102, 104 independently receives and secures a bar, pin or other fixation element. Other embodiments of the clamping device 100 include only a single bar or pin clamp on one end, with a multi-clamp set or other arrangement on the other end.

The bar clamps 102, 104 of the clamping assembly 100 provide multiple degrees of freedom, each operating independently of the other. For example, each clamp may pivot about a roll axis, a pitch axis, and a yaw axis in the clamp 102, 104. The roll axis is the axis of a bar or other fixation element within the clamps and about which the clamping device 100 may rotate. The pitch axis is a transverse axis about which the outer and inner jaws rotate relative to saddle components and/or the rest of the clamping assembly. The yaw axis is a longitudinal axis 107 defined by a post component or stud 108 and about which the clamp 102 can rotate relative to the clamp 104. The clamping assembly 100 is tightened onto a fixation element, and the clamp 102 is tightened to clamp 104 through tightening of a washer 112, a nut 114 and the post component 108 (all in FIG. 2), although other tightening methods are contemplated. The post component 108 includes a head (the top being visible in FIG. 2) and a shaft that extends through the clamping assembly to connect with the nut 106. The head of the post component 108 may be formed with a bowl-like surface shape, such as a spherical surface shape for example, that matches the spherical shape of the washer 112, which can be seen in FIG. 3. In some embodiments, the post component does not include a head, but has two threaded ends that cooperate with two nuts for tightening the clamping assembly 100. Additional description of the axes and a post component or stud can be found in U.S. patent application Ser. No. 13/271,744 to Mullaney, filed Oct. 12, 2011, incorporated herein by reference. As used herein, the clamping side of each clamp 102, 104 is intended to mean the side of the clamp that receives the fixation element and the rearward side is the side opposite the side of the clamp receiving the fixation element. In FIG. 2, the clamping side of the clamp 102 is on the left and the clamping side of the clamp 104 is on the right.

Figure 4A:
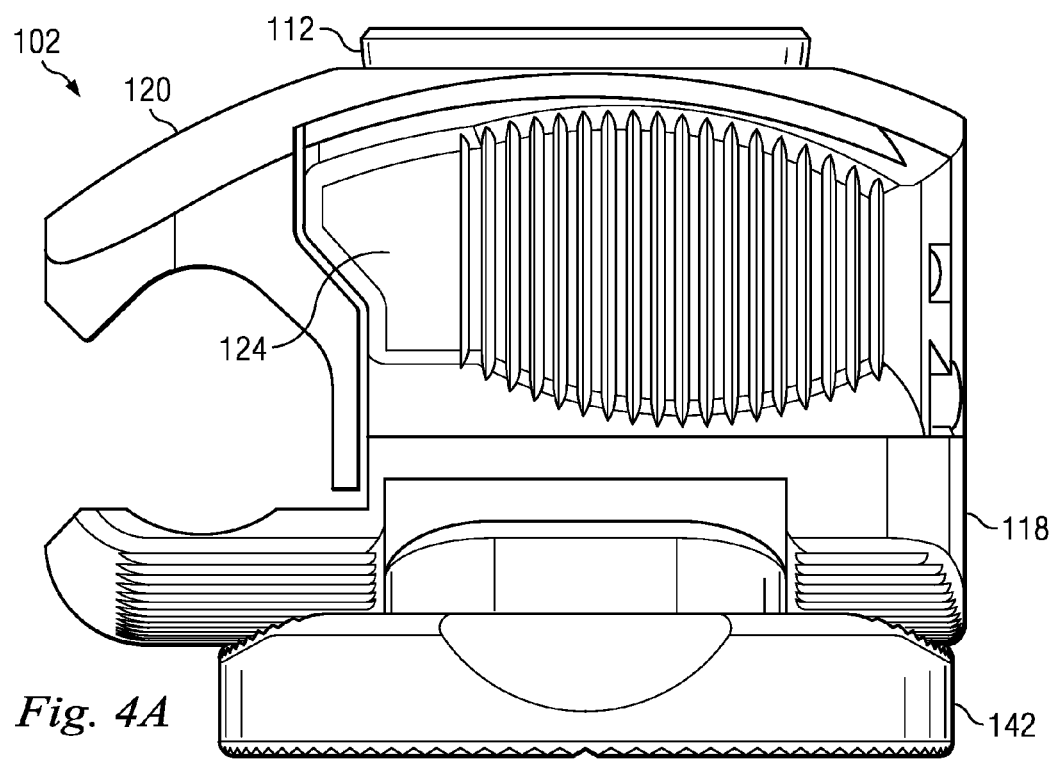
FIGS. 4A-4C are illustrations of the clamp of FIG. 3 showing a side view, a top view, and a back view respectively.
Figure 4B:
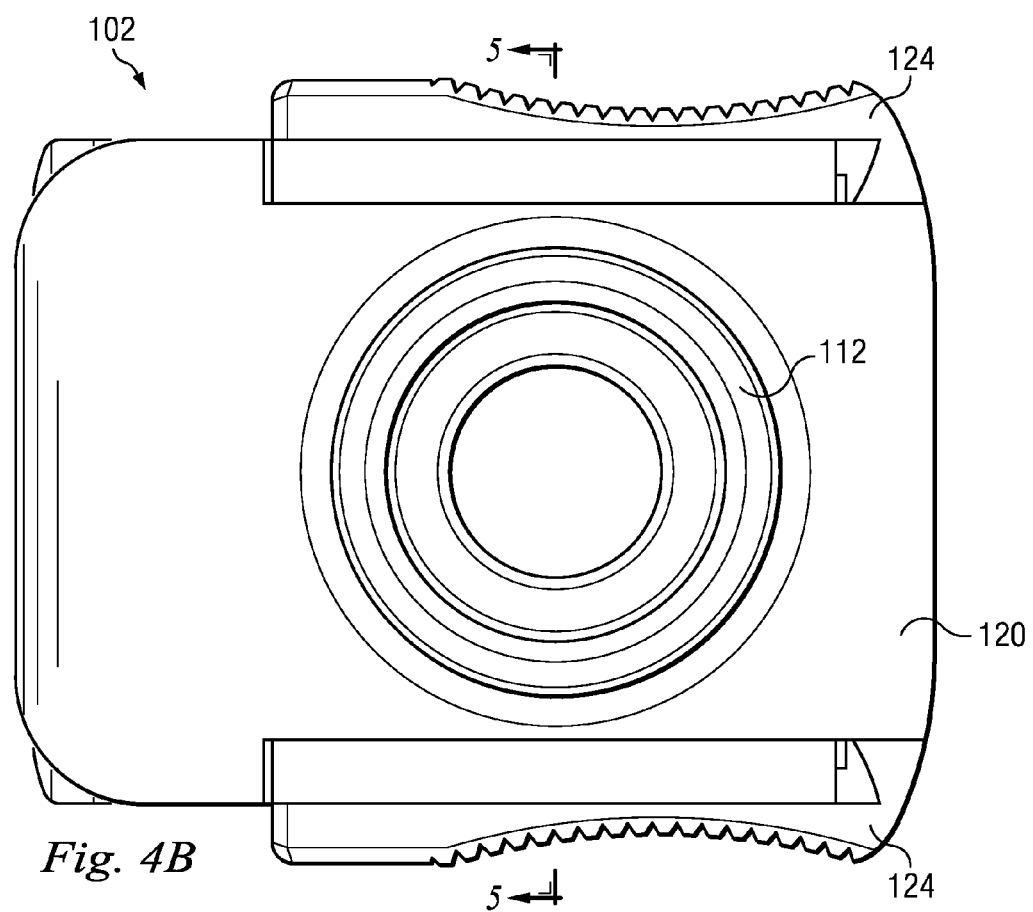
Figure 4C:
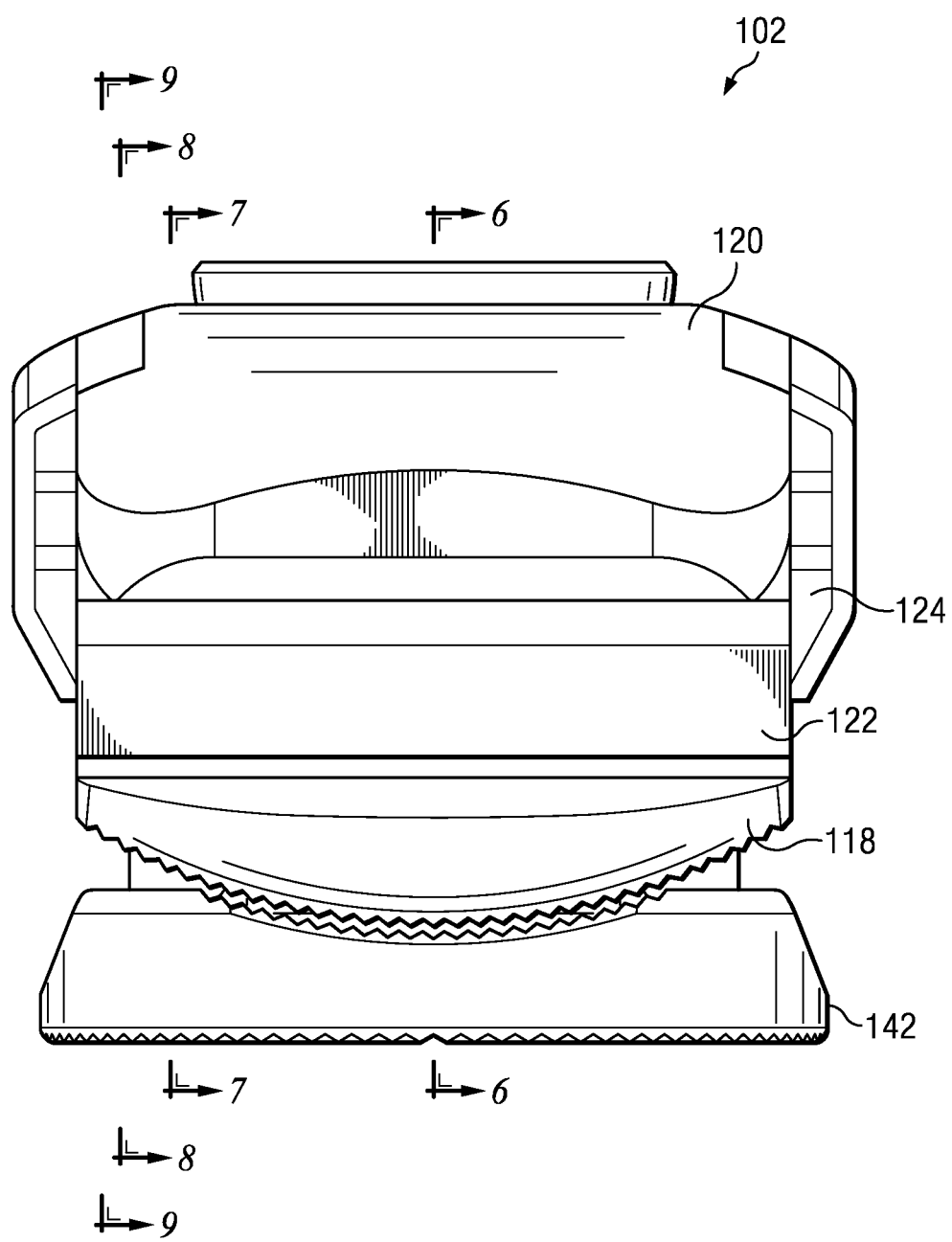

FIG. 2 shows a side view of the clamping assembly 100 and FIG. 3 shows an exploded view of the clamp 102. FIGS. 4A-4C respectively show a side view, a top view, and a rear view. FIGS. 5-9 are cross-sectional views taken through the respective lines 5-5, 6-6, 7-7, 8-8, and 9-9 in FIGS. 4B and 4C. Referring now to FIG. 3, the clamp 102 includes an inner jaw 118 and an outer jaw 120. These jaws cooperate to capture the fixation element therebetween.

Referring to FIG. 3, the clamp 102 also includes a latch 122, cam sliders 124, guide pins 128, sliding pins 130, and stop pins 132. The clamp 102 also includes coil springs 134, and balls 136. In addition, the clamp includes a spacer 138, a spring washer 140, and a saddle 142. Detailed descriptions of the spacer 138, the spring washer 140, and the saddle 142 may be found in incorporated U.S. patent application Ser. No. 13/271,744, and therefore, they will not be described further here. It should be noted that the spacer 138, the spring washer 140, and the saddle 142 are not required to be part of the clamp, but are in place to provide an extra degree of articulation for each of the clamps 102 and 104. In some embodiments, these components are not present in the clamping assembly 100, and the inner jaw 118 of each of the clamps 102, 104 is configured to bear against the opposing inner jaw directly, removing the extra degree of freedom. In other embodiments, alternative pivoting elements provide the extra degree of freedom.

In the embodiment shown, each of the inner and outer jaws 118, 120 include respective grooves or concave recesses 146, 148 for capturing the fixation element. The recesses 146, 148 may be shaped to generally correspond to the profile of the fixation elements, or may have shapes different than the profiles of the fixation elements. In some examples, the recesses 146, 148 are configured to contact the fixation element at only particular locations, such as two locations each. In addition, in some embodiments, the recesses include teeth, cut-outs, or other features that interface with bars having a non-smooth or non-circular outer surface. In some examples, the jaws include flats on one or more of the jaws in place of the concave recesses.

The inner jaw 118 is configured and arranged with a base portion 152 and two extending wall portions 154. The base portion 152 includes a through hole 156 configured to receive the post component 108, and in one embodiment, may allow the clamp 102 to pivot around the post component 108. It may also be shaped to allow the clamp 102 to rotate or pivot relative to the post component 108. Thus, the through hole 156 may have a rectangular shape, with rounded ends as shown in FIG. 3 and may include a conical component as shown in the cross-sectional view of FIG. 5. In other embodiments, the through hole 156 cooperates with the post component 108 to restrict relative rotation, while the clamp 104 and/or post component 108 is configured to permit relative rotation. In such an embodiment, the clamp 104 may rotate about the post component relative to both the post component 108 and the clamp 102 in the manner described in incorporated U.S. patent application Ser. No. 13/271,744. The wall portions 154 extend in substantially parallel planes from the base portion 152, with each wall portion 154 including an inner surface 158 and an outer surface 160. The inner surface 158 includes a groove 162 extending along at least a portion of its length configured to receive a ball 136, a coil spring 134, and a stop pin 132. This groove 162 is configured to cooperate with these elements to limit the movement of the latch 122 relative to the inner jaw 118. Dove-tail grooves 163 are formed in the outer surface 160 of the wall portions 154. These transversely extending grooves are arranged to receive and connect with the cam sliders 124 in the manner discussed below.

Each of the wall portions 154 include guide slots 164 formed on the inner surface 158. In this embodiment, the angled slots extend through the wall portions from the inner surface 158 to the outer surface 160, and also extend into the drove tailed groove 163. Here, the guide slots 164 are angled with one end of each slot at a lower elevation and the other end of each slot at a higher elevation. These guide slots 164 will guide the movement of the upper jaw as will become apparent from the discussion further below.

Figure 5:
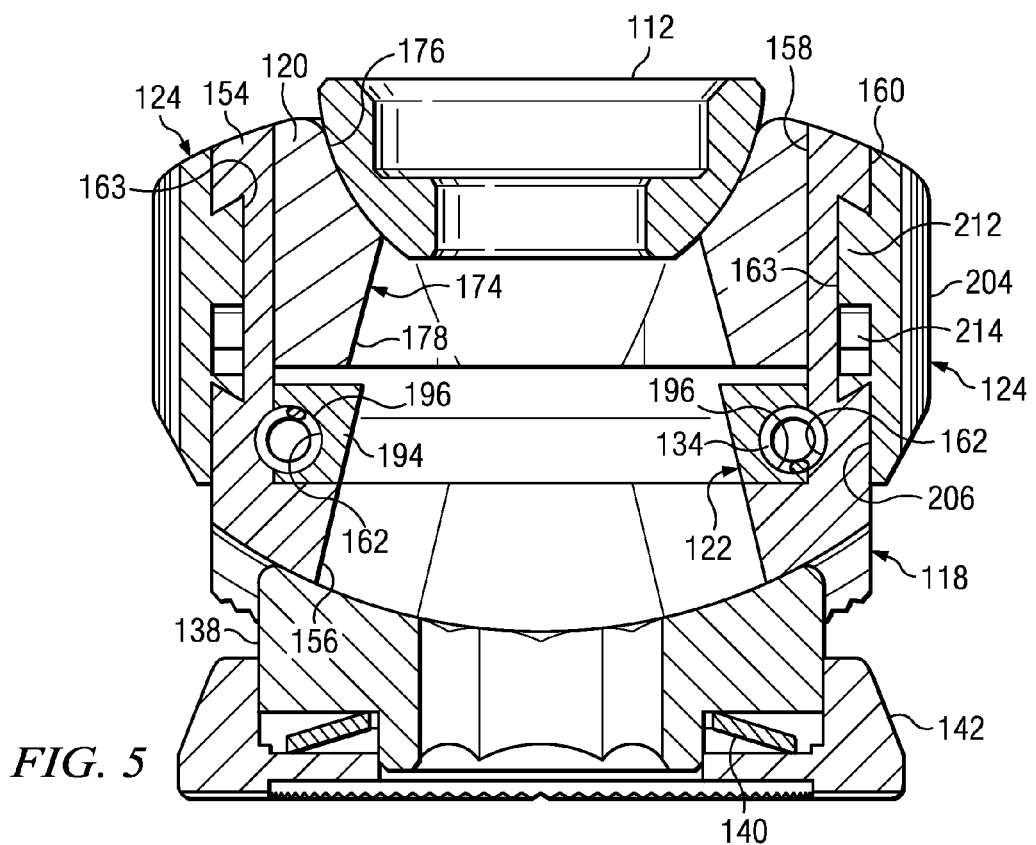
FIG. 5 is an illustration of a cross-section of the clamp of FIG. 4B taken through the lines 5-5 in FIG. 4B according to one exemplary aspect of the present disclosure.

The outer jaw 120 is sized with a body portion 170 and a head portion 172. The head portion 172 includes the rod-receiving recess 148. The body portion 170 has a width sized to fit between the wall portions 154 in the inner jaw 118, as can be seen in FIG. 5. It includes a through hole 174 with a spherical top portion 176 and a rectangular, but conically shaped bottom portion 178, that can be seen in FIG. 5. The spherical top portion 176 is arranged to cooperate and receive the spherical washer 112. Four bore holes 180 are formed into sides of the body portion 170 for receiving the guide pins 128. A shoulder portion 182 separates the head portion 172 and the body portion 170. It projects out from the body portion 170 and may form a mechanical stop surface for the cam sliders 124. The outer jaw 120 also includes a back stop 184 adjacent the rod-receiving recess 148. The back stop 184 cooperates with a fixation element as it is introduced into the clamp 102, as will be explained below.

The outer jaw 120 is received into and held within the inner jaw 118. The guide pins 128, of which four are shown are pressed into the bore holes 180 through the guide slots 164 and act to retain the outer jaw 120 within the inner jaw 118 and effect movement of the outer jaw 120 relative to the inner jaw 118 as explained below. This can be seen in the cross-sectional view in FIG. 8. The curvature of the guide slots 164 in the inner jaw 118 is such that the center of rotation is generally about the same center as the spherical bore 166 formed in the outer jaw 120 although slight discrepancies from the center of rotation might be desirable in some embodiments. As will become apparent from the discussion below, the guide pins 128 travel along the guide slots 164 to effect movement of the upper jaw 120 relative to the lower jaw 118. In accordance with this, the width of the guide slots 164 in relationship to the diameter of the guide pins 128 is determined based on the travel requirements of the outer jaw 120 relative to the inner jaw 118 to insure that adequate clamping force can be applied to the fixation element. Accordingly, these guide slots 164 may have a width larger or smaller than that shown in order to permit the jaws 118, 120 to suitably clamp onto a particularly sized fixation element, whether a bone pin, fixation rod or other fixation element.

The latch 122 extends into the inner jaw 118 and is configured to be disposed, at least in part, between the inner and outer jaws 118, 120. As will become apparent from the discussion below, the latch 122 moves forward and aft between the jaws 118, 120 to wedge the outer jaw 120 into a closed position that secures a fixation element within the clamp 102.

In this embodiment, the latch 122 is formed in an L-shape, with a substantially horizontal portion 190 and a substantially vertical portion 192. The substantially horizontal portion 190 is bifurcated with two legs 194 formed by a central cut-out portion. The cut-out portion accommodates the post component 108 extending through the clamp 102. Each of the legs 194 includes a groove 196 extending along at least a portion of the legs 194. When the latch 122 is disposed in place between the wall portions 154 of the inner jaw 118, the latch grooves 196 at least partially overlap with the grooves 162 in the inner surface 158 of the wall portions 154. The ball 136, the coil spring 134, and the stop pins 132 are disposed in both the grooves 162 and the grooves 196 and cooperate to bias the latch 122 toward the receiving-half of the clamp 102. That is, the coil spring 134 pushes the ball 136 toward the closed end of the groove 162 in the legs 194. Likewise, the spring 134 pushes the stop pin 132 toward the closed end of the groove 162. The net forces cooperate to bias the latch toward a location where the substantially vertical portion is between the inner and outer jaws 118, 120.

Figure 6:
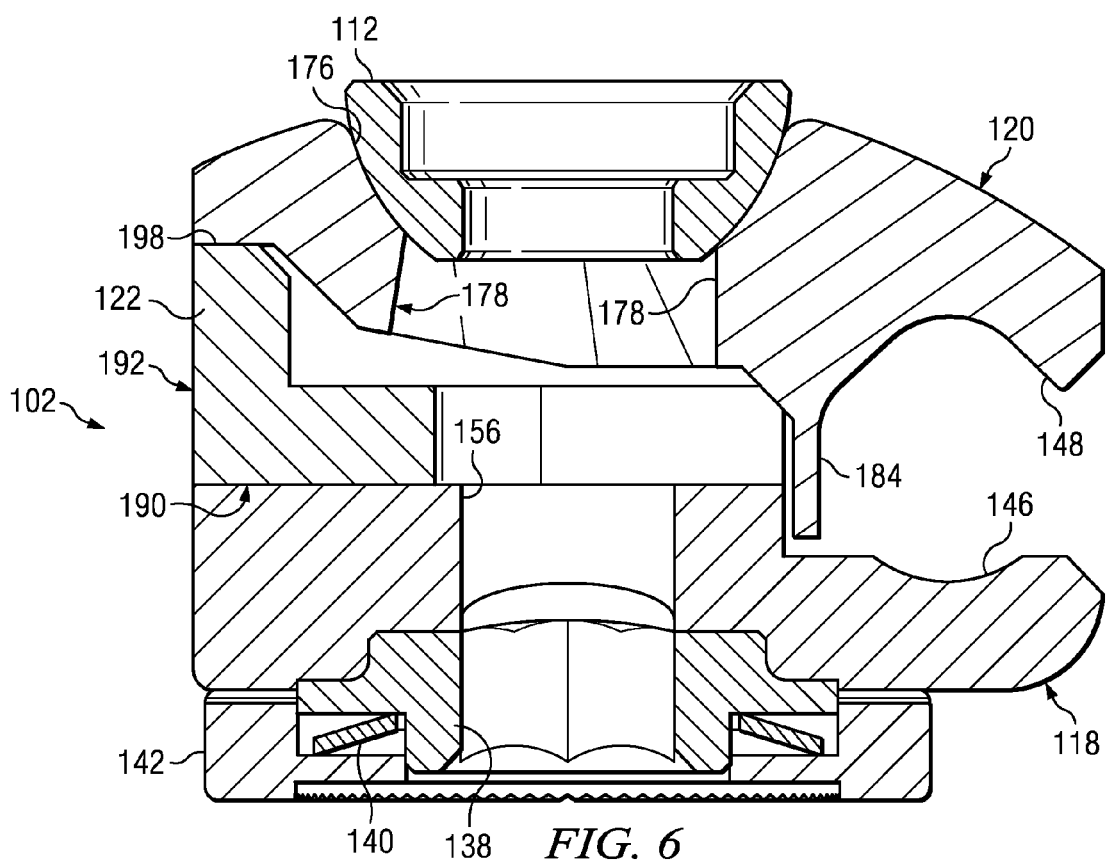
FIG. 6 is an illustration of a cross-section of the clamp of FIG. 4C taken through the lines 6-6 in FIG. 4C according to one exemplary aspect of the present disclosure.

The substantially vertical portion 192 of the latch 122 is a blocking element having an upwardly facing surface 198 at the top of the latch 122 configured to interface with the inner surface of the upper jaw 120 and physically limit its ability to pivot around the spherical washer 112, preventing displacement that would allow removal of a fixation element that will be contained between the inner and outer jaws 118, 120. This is shown in FIG. 6. With the latch 122 disposed underneath the outer jaw 120, the back end of the outer jaw 120 is mechanically prevented from rotating toward the inner jaw 118. Since the spherical washer 112 and nut 114 prevent the front of the outer jaw 120 from pivoting upward when the rearward end cannot pivot downward, the outer jaw 120 is unable to pivot sufficiently to open to receive or release a fixation element. Accordingly, FIG. 6 shows the clamp in a closed position. Since the ball 136 abuts the end of the groove 196 formed in the latch 122, and since the stop pin 132 abuts an end of the corresponding groove 162 in the inner jaw 118, the latch is biased toward this locked position. This can be seen in the cross-sectional view of FIG. 6. Bores 200 are formed into sides of the substantially vertical portion 192 of the latch 122. These bores 200 are configured to receive the stop pins 132. These pins may be press fit with an interference that secures the stop pins 132 in the bores 200, may be adhered with a cement or other adhesive, or may be otherwise formed or attached to the latch 122.

Figure 7:
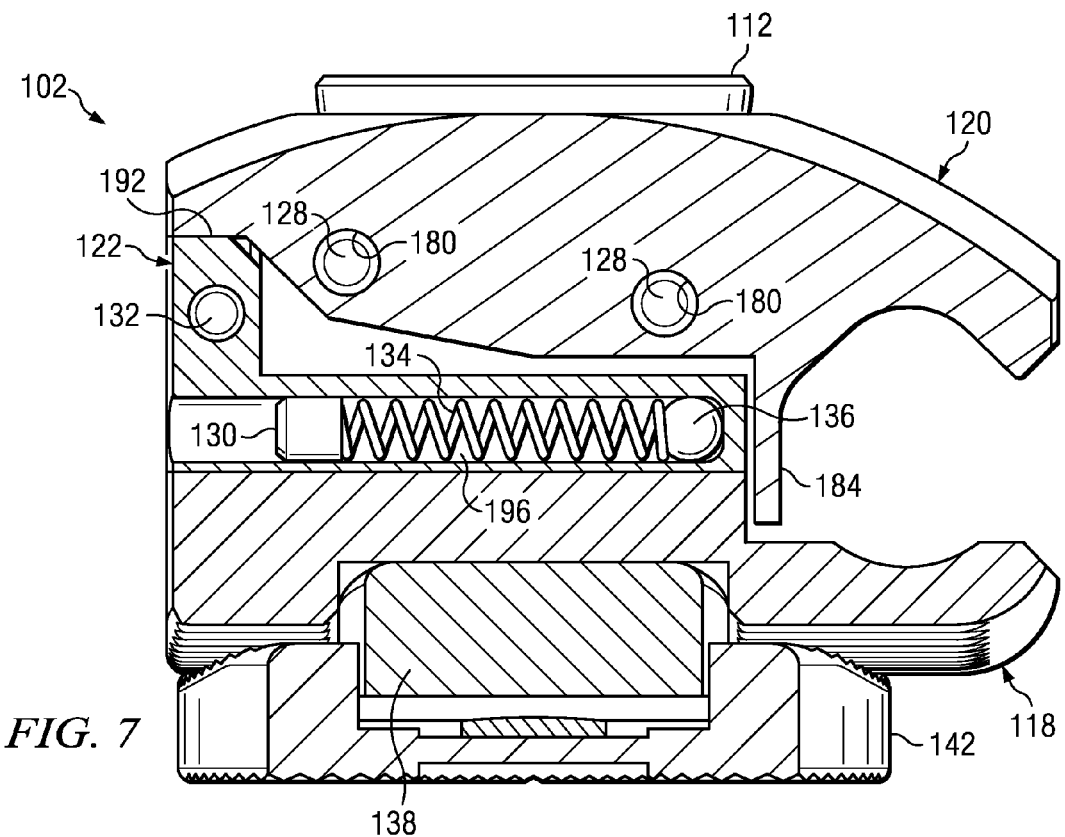
FIG. 7 is an illustration of a cross-section of the clamp of FIG. 4C taken through the lines 7-7 in FIG. 4C according to one exemplary aspect of the present disclosure.
Figure 8:
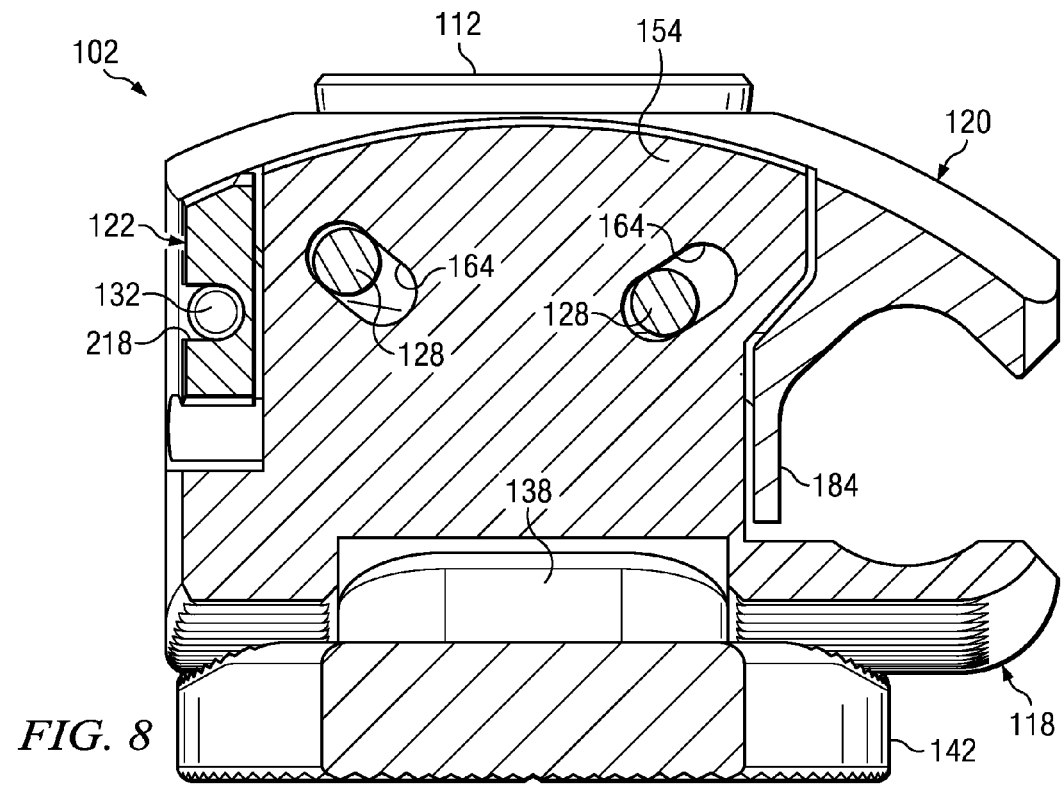
FIG. 8 is an illustration of a cross-section of the clamp of FIG. 4C taken through the lines 8-8 in FIG. 4C according to one exemplary aspect of the present disclosure.
Figure 9:
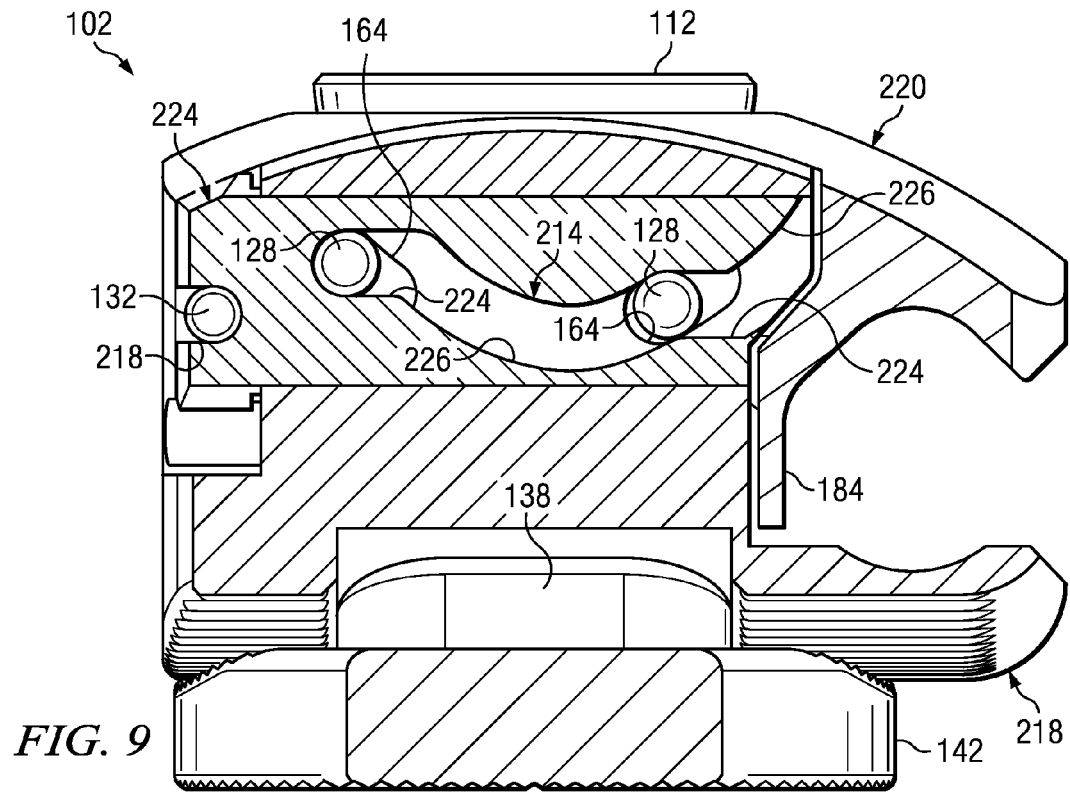
FIG. 9 is an illustration of a cross-section of the clamp of FIG. 4C taken through the lines 9-9 in FIG. 4C according to one exemplary aspect of the present disclosure.

FIGS. 5-9, corresponding to cross-sections 5-5 through 9-9 in FIGS. 4B and 4C, show the latch 122 in a fully engaged position wedging the outer jaw 120 into the closed position. As can be seen, the upwardly facing surface 198 of the latch 122 is engaged with the lower surface of the outer jaw 120 at the rearward side of the clamp 102. This position is a provisional locking condition, with the inner and outer jaws 118, 120 configured to prevent opening of the jaws and preventing removal or insertion of a fixation element between the jaws. To maintain this position, and as shown in FIG. 7, the coil spring 134 compresses ball 136 into the forward end of the groove 196 and bears against the stop pin 132 which bears against the end of the groove 162 (FIG. 2) in the inner jaw 118, acting to bias the latch 122 into the engaged position. It should be noted that the ball 136 and the cylinder stop pin 132 are optional components that may provide for ease of manufacturing and to ensure an adequate bearing surface for the coil spring 134.

The cam sliders 124 are disposed in and run along the wall portions 154 in the dovetail grooves 163 formed in the outer surface 160 of the wall portions 154. This can be best seen in the cross-sectional view of FIG. 5, but also shown in the exploded view of FIG. 3. In this embodiment, the cam sliders 124 are independent of each other, and each has an outer facing surface 204, an inner facing surface 206 that faces the wall portions 154 of the inner jaw 118, a leading end 208 configured to match with and engage the shoulder portion 182, and a trailing end 210. In the example shown, the outer facing surface 196 includes finger depressions formed therein for gripping by a user to slide the cam slider within the dove-tail groove 163 of the inner jaw wall portions 154. The inner facing surface 198 includes the dove-tailed feature 212 configured to match the dove-tailed groove 163 in the inner jaw 118, includes a milled guide cam slot 214 formed in the dovetailed feature (best seen in FIGS. 3 and 9), includes a protruding stop portion 216 at the trailing end 202, and includes a stop pin interface slot 218 formed in the protruding stop portion 216.

The stop pin interface slot 218 is open at the trailing end 210 of the cam slider 124 and is disposed to receive and engage the stop pin 132 which is carried in the bore 200 on the latch 122. The open end of the stop pin interface slot 218 allows the cam sliders 124 to pull back and displace the latch 122 relative to the inner jaw 118, but have no effect on the latch 122 when the cam sliders 124 are pushed forward. This decoupling of the cam sliders 124 from the latch 122 allows the latch 122 to operate independently when traversing from the open (unlatched) position to the closed (latched) position. The milled guide cam slot 214 (labeled in FIG. 3) is formed in the cam slider 124 in a position that accepts the guide pins 128, as they extend through the guide slots 164 of the inner jaw 118 and into the bore holes 180 in the outer jaw 120. These guide cam slots 214 control the rotation of outer jaw 120 as a function of the position of the cam slider. Depending on the embodiment and the size of the fixation element to be grasped, this function can be tailored to provide a wide variety of motion and mechanical advantage as would be desired.

As can be seen, the guide cam slot 214, in this embodiment, includes an irregular surface having flat portions 224 and curved portions 226. The guide cam slot 214, along with the flat and curved portions, guide the movement of the upper jaw 120 relative to the inner jaw 118 to open and close the clamp 102. Although two flat portions and two curved portions are shown, other embodiments include only one flat portion while yet others include no flat portions. Additional flats or curves may be included to guide the movement of the upper jaw relative to the lower jaw to open and close the clamp 102 as will be described below.

Figure 10A:
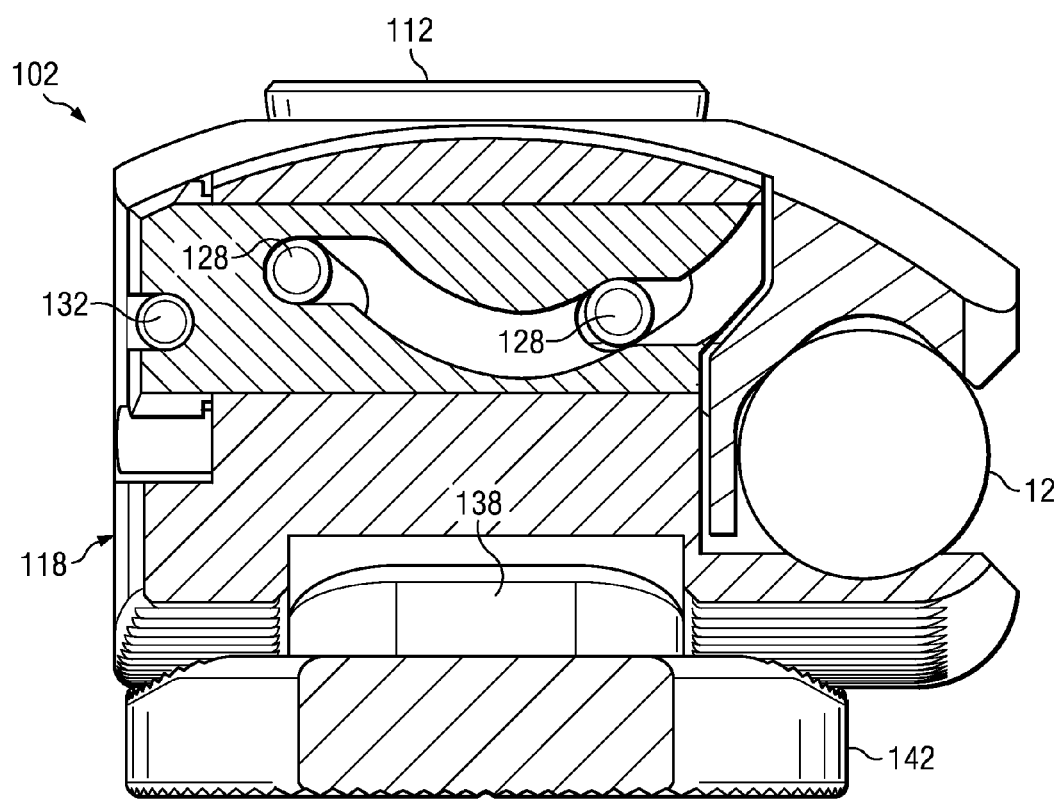
FIGS. 10A-10C are a series of illustrations of a cross-section of the clamp of FIG. 4C taken along the lines 9-9, showing a cam slider in various positions as an upper jaw displaces relative to a lower jaw to capture or release a fixation element according to one exemplary aspect of the present disclosure.
Figure 10B:
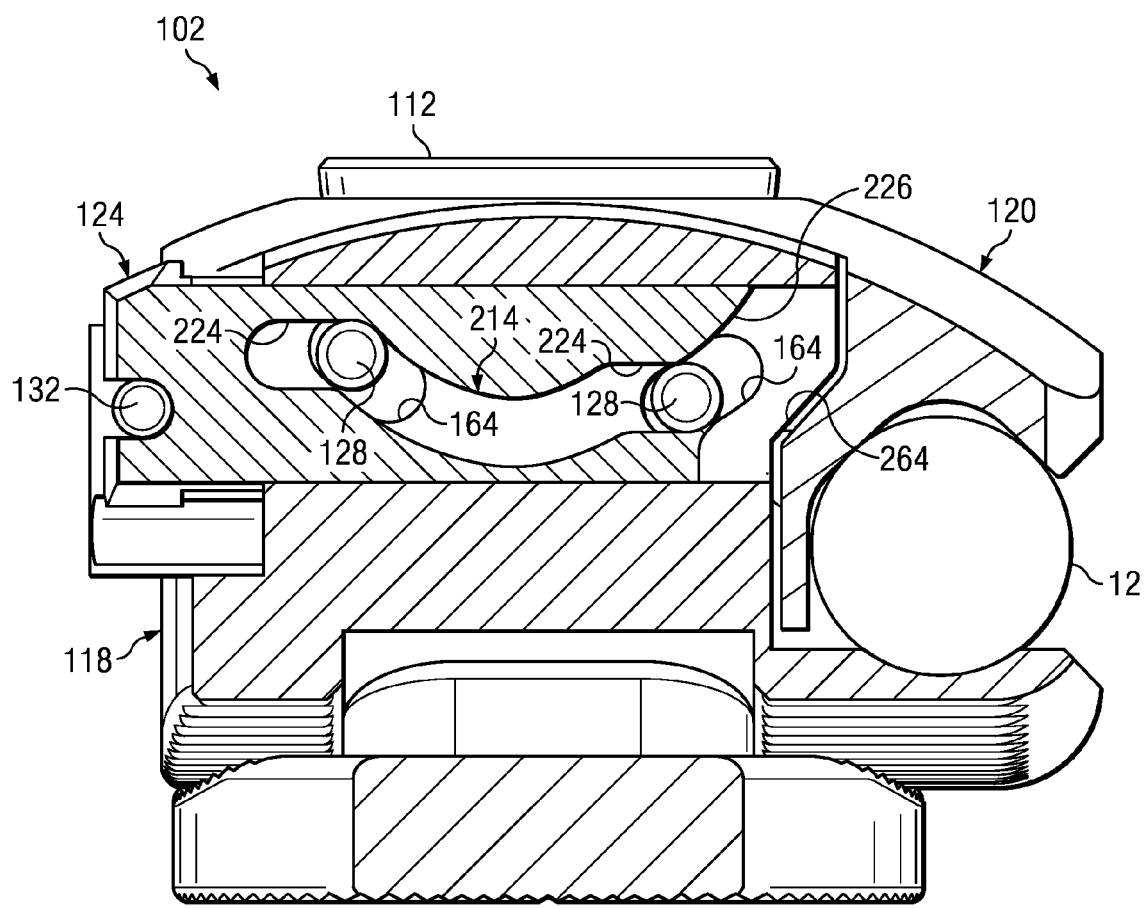
Figure 10C:
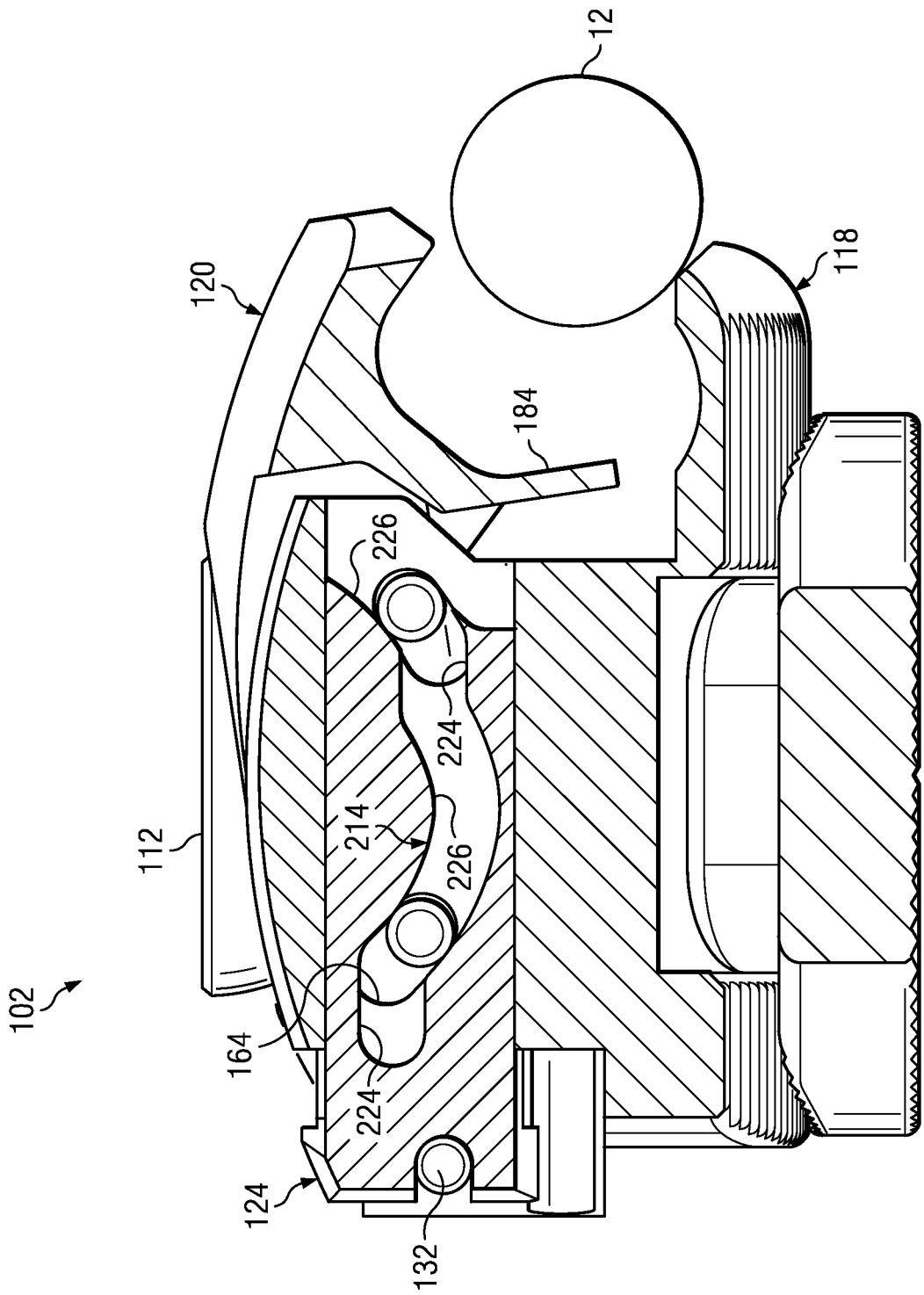

FIGS. 10A-10C depict an operational sequence of opening the clamp 102 to either capture or release a fixation element. The cross-section is taken through lines 9-9 in FIG. 4C. Accordingly, FIG. 10A is similar to FIG. 9, with the clamp 102 in a closed position, but includes a fixation element referenced by the numeral 12. The cross-sectional view in FIGS. 10A-10C through one of the cam sliders 124 shows the interaction between the guide cam slot 214 in the cam slider 124, the guide slots 164 in the inner jaw 118, and the guide pins 128 fixed on the upper jaw 120 to open and close the clamp 102. Here, FIG. 10A shows the clamp in the closed position. FIG. 10B shows the cam sliders 124 in a pulled back condition, thereby displacing the latch 122 from underneath the outer jaw 120 and beginning to move rearwardly such that the guide pins 128 are leaving the flat portion 224 of the milled guide slots 124. The flat portion 224 ensures that the outer jaw 120 can be locked in place. In FIG. 10C, the guide pins 128 are being forced into the curved portion 226 of the milled guide cam slot 214 effectively raising the front of the outer jaw 120 and effectively lowering the rear of the outer jaw 120 as it pivots about the spherical washer to open the clamp 102.

These processes for accomplishing locking onto a fixation element and releasing a fixation element will be described in greater detail. Starting with FIG. 10A, the cam slider 124 is in a neutral position, with the stop pin 132 disposed in the flat or linear portion 224 of the guide cam slot 214. The balls 136, the coil springs 134, and the sliding pins 130 are disposed in the grooves 196 in the latch 122 and in the groove 162 in the inner jaw 118. The biasing force from the spring 134 acts against the ends of the groove 196 and the groove 162 to bias the latch 122 to a position where it physically interferes with and limits the rotational pivot range of the outer jaw 120. This is the position shown in FIG. 6, with the upwardly facing surface or the uppermost surface 198 of the latch 122 interfacing with an inner surface of the upper jaw 120, and restricting its ability to pivot about the spherical washer 112 relative to the inner jaw 118. Accordingly in this position, the clamp 102 is in a provisionally locked state, where the clamp 102 cannot be opened to remove the fixation element 12 shown in FIG. 10A. In this condition, the clamp 102 may be loose enough on the fixation element 12 to permit spinning about the fixation element or sliding along the fixation element as the surgeon continues to construct the fixation frame or fixation system.

In order to open the clamp 102, to either receive or remove the fixation element, the surgeon or health care provider must displace the cam sliders 124 rearwardly relative to the inner and outer jaws 118, 120. Accordingly, the surgeon may grip the cam sliders 124 along their gripping portions on the outer facing surfaces 204 using a thumb and fingers, and move the cam sliders 124 rearwardly, away from the clamping side of the clamp 102. Rearward displacement of the cam sliders 124 causes the milled stop pin interface slots 218 in the cam sliders 124 to apply a displacement force on the stop pins 132 that are fixed into the latch 122, forcing the latch 122 to move rearwardly with the cam sliders 124. Accordingly, rearward displacement of the cam sliders 124 results in displacement of the latch 122. This movement is against the biasing force of the coil spring 134, which compresses in the grooves 162, 196. As the latch 122 moves rearwardly, the upper surface 198 of the latch 122 moves rearwardly beyond the inner surface of the outer jaw 120. This frees up the outer jaw 120 to pivot about the spherical washer 112 to move relative to the inner jaw 118, subject to the guide pins 128, the guide slots 164, and the cam slider guide cam slot 214. As the cam sliders 124 are displaced relative to the outer jaw 120, they are also displaced relative to the guide pins 128 that are fixed into the outer jaw 120. Further displacement of the cam sliders 124 relative to the guide pins 128 (and the outer jaw 120) causes the guide pins 128 to move from the linear region or flat portion 224 of the guide cam slot 214 into the arcuate region or curved portion 226, as shown in FIG. 10B. Because the cam slider movement is limited to linear movement by the dove-tail attachment to the lower jaw 118, movement of the cam slider 124 causes a vertical reactionary movement on the guide pins 128 of the outer jaw 120. This force causes the guide pins 128 to move along the guide slots 164 in the inner jaw 118 (best seen in FIG. 3, but visible in FIGS. 10B and 10C) in a manner that forces the outer jaw 120 to displace relative to the inner jaw 118, opening in the manner shown in FIG. 10C. To open, the outer jaw 120 pivots around the spherical washer 112. The slots 164 in the inner jaw 118 and the cam slots 214 in the cam slider 124 are sized and arranged to open the jaws of the clamp 102 a particular distance, to receive a particularly sized fixation element. Accordingly, certain clamp embodiments will be arranged to receive the bone pins 14 in FIG. 1, while other clamp embodiments will be arranged to receive the external fixation rods 12. The shapes can be formed to fit any size of fixation element.

With the clamp 102 in the open position shown in FIG. 10C, the clamp is ready to receive the fixation element. In this position, even if the operator releases the cam slider 124, the clamp 102 is maintained in the open position. This is because the outer jaw 120 has pivoted about the spherical washer 112 so that the rearward side of the jaw 120 is below the uppermost upwardly facing surface 196 of the latch 122. With the latch 122 still biased toward to the open end of the clamp 102, the substantially vertical portion is behind the outer jaw, rather than between the outer and inner jaws 120, 118. That is, while it may abut against the rearward end of the outer jaw 120, the latch's forward movement is physically blocked by the location of the rearward end of the outer jaw 120. As such, until the outer jaw 120 rotates, the biased latch cannot move further between the jaws 118, 120. Accordingly, in this position, the latch is effectively cocked and the clamp is ready to snap onto a fixation element. When the fixation element is introduced between the open jaws, it may be placed within the passage between the open jaws. Upon further advancement, the fixation element comes into contact with the backstop 184 on the outer jaw 120 and further advancement causes the outer jaw 120 to pivot about the spherical washer, with the front end of the jaw moving toward the inner jaw 118 and the rearward end of the jaw moving away from the inner jaw 118. When the rearward end of the outer jaw 118 clears the latch 122, the latch advances due to the biasing force of the springs 134 to the position shown in FIG. 7. The stop pins 132 in the bores 200 on the latch engage the stop pin interface slots 218 on the cam sliders 124 and likewise advance the cam sliders 124 with the advancing latch 122. In this position, and as explained above, the clamp 102 is in the provisionally locked state and the fixation element cannot be removed from the clamp 102. Accordingly, the fixation element is captured in the manner shown in FIG. 10A.

With the fixation element 12 provisionally locked in the clamp 102, the clamping assembly 100 can be rigidly locked on the fixation element 12 by applying a clamping load with the inner and outer jaws 118, 120 onto the fixation element 12. As indicated above, in this embodiment, the stud or post component 108 and the nut 106 cooperate to pass entirely through the clamping assembly 100. Tightening the nut 106 lessens the distance between the nut 106 and the head of the post component 108 shown in FIG. 2. This lessening of that distance forces the spherical washer 112 against the outer jaw 120 which in turn forces the outer jaw 120 closer to the inner jaw 118, tightening the construct on the fixation element. The guide slots 164 are formed and shaped to permit this downward displacement of the outer jaw 120 relative to the inner jaw 118. Because the rearward portion of the outer jaw 120 cannot displace further toward the inner jaw 118 because of the latch 122, the displacement occurs primarily at the clamping side, increasing the clamping load on the fixation element 12 in the receiving-recesses 146, 148. In addition, the spring washer 140 opposes this displacement. The tightening causes the spring washer 140 to compress, locking the inner jaw 118 into serrations on the saddle 142, and locking serrations on the saddles of the opposing clamps 102, 104 to each other. In one embodiment, the spring rate is tailored to allow for a variable amount of friction as a function of nut torque such that the resistance to motion of the fixation element 12 can be adjusted to facilitate gross manipulation of the jaws 118, 120 relative to the saddle 142 and the saddles 142 of each clamp 102, 104 relative to each other without such a high degree of force being applied such that the serrations on the saddle 142 become engaged with the opposing serrations on the inner jaws 118. To facilitate this action a high rate spring washer 140 may be used between the saddle 142 and its mating inner jaw 118. Accordingly, positively clamping on the fixation element 12 forces the spring washer 140 to collapse, thereby allowing the serrations on opposing saddles 142 and on the inner jaws 118 to come into engagement positively locking the construct in a fixed state.

The guided cam action both increases and decreases the size of the bar-receiving opening. Accordingly, the clamp does not rely upon a longitudinal spring pressure or biasing force to open and close the jaws or to place the jaws in a provisionally locked state from an open state. Instead, the jaws are guided into the open position and the provisionally locked position via the guide slots that act as a track that guides and directs the movement of the jaws relative to each other.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A clamping assembly configured to secure a fixation element of an external fixation assembly, comprising:
   a first jaw comprising at least one projection;
   a second jaw operatively connected to the first jaw by at least one aperture in the second jaw in which the at least one projection is received, the first and second jaws being cooperatively positioned to receive the fixation element therebetween; and
   a sliding cam slidably attached to the second jaw, the sliding cam having a guide cam slot engaging the at least one projection of the first jaw, wherein moving the sliding cam relative to the second jaw moves the first jaw relative to the second jaw from an open condition for receiving the fixation element between the jaws to a clamping condition for capturing the fixation element between the jaws.

2. The clamping assembly of claim 1, further comprising a latch selectively disposed between the first and second jaws, the latch being moveable relative to the first and second jaws to position a wedge portion of the latch between respective portions of the first and the second jaws to physically limit the range the first jaw can travel relative to the second jaw to secure the first and second jaws in the clamping condition.

3. The clamping assembly of claim 1, wherein the guide cam slot includes an arcuate portion and a linear portion.

4. The clamping assembly of claim 1, wherein the second jaw comprises wall portions, the first jaw being disposed between the wall portions, the sliding cam being slidably attached to the wall portions.

5. The clamping assembly of claim 4, further comprising a latch selectively disposed between the first and second jaws, the latch being moveable relative to the first and second jaws to position a wedge portion of the latch between respective portions of the first and the second jaws to physically limit the range the first jaw can travel relative to the second jaw to secure the first and second jaws in the clamping condition.

6. The clamping assembly of claim 5, wherein the latch is disposed between the wall portions.

7. The clamping assembly of claim 6, wherein the latch comprises an L-shape comprising:
   a first portion; and
   a second portion extending perpendicularly from the first portion, the second portion being divided into two legs by an aperture in the second portion.

8. The clamping assembly of claim 7, wherein the first portion of the latch comprises the wedge portion.

9. The clamping assembly of claim 8, wherein the two legs of the second portion of the latch are respectively operatively attached to the walls of the second jaw via a biasing element, the biasing element acting to bias the wedge portion of the latch between respective portions of the first and the second jaws to physically limit the range the first jaw can travel relative to the second jaw to secure the first and second jaws in the clamping condition.

10. The clamping assembly of claim 9, wherein the latch is arranged relative to the first and second jaws such that the wedge portion of the latch is positioned adjacent respective aft ends of the first and second jaws and respective ends of the two legs of the second portion of the latch are positioned adjacent respective forward ends of the first and second jaws, and the latch being moveable relative to the first and second jaws to position the wedge portion of the latch between the respective aft ends of the first and the second jaws to physically limit the range the first jaw can travel relative to the second jaw to secure the first and second jaws in the clamping condition.

11. The clamping assembly of claim 10, wherein the sliding cam is configured to slide between the respective forward and aft ends of the first and second jaws, the latch being operatively attached to the sliding cam such that only movement of the sliding cam toward the respective forward ends of the first and second jaws causes the latch to move relative to the first and second jaws.

12. The clamping assembly of claim 4, wherein the second jaw comprises two wall portions, the sliding cam comprising:
   a first cam slider slidably attached to one of the two wall portions; and
   a second cam slider slidably attached to the other of the two wall portions.

13. The clamping assembly of claim 12, wherein the first and second cam sliders are slidably attached to the two wall portions by respective dovetail grooves in each of the two wall portions.

14. The clamping assembly of claim 12, wherein the first and second cam sliders are slidably attached to the two wall portions by respective dovetail grooves in each of the two wall portions.

15. The clamping assembly of claim 4, wherein the second jaw comprises two wall portions, the sliding cam comprising:
   a first cam slider slidably attached to one of the two wall portions; and
   a second cam slider slidably attached to the other of the two wall portions.

16. The clamping assembly of claim 1, further comprising a biasing member that acts to bias the first jaw toward the clamping condition.

17. The clamping assembly of claim 1, wherein the second jaw includes a wall portion having at least one aperture formed therein, the projection received in the at least one aperture of the wall portion of the second jaw and the guide cam slot, and the aperture of the wall portion of the second jaw and the guide cam slot being configured to guide displacement of the first jaw relative to the second jaw from the open condition to the clamping condition.

18. The clamping assembly of claim 17, wherein the first jaw has a curved bore portion, and wherein the aperture of the wall portion of the second jaw is curved and disposed to have a center coincident with a center of the curved bore portion.

19. The clamping assembly of claim 18, wherein the curved bore portion comprises a semi-spherical bore.

20. The clamping assembly of claim 1, wherein the guide cam slot is configured to force the first jaw to vertically displace relative to the second jaw.

21. A clamping assembly configured to secure fixation elements of an external fixation assembly, comprising:
a first clamp comprising:
a first jaw comprising at least one projection;
a second jaw operatively connected to the first jaw by at least one aperture in the second jaw in which the at least one projection is received, the first and second jaws being cooperatively positioned to receive a first fixation element therebetween; and
a sliding cam slidably attached to the second jaw, the sliding cam having a guide cam slot engaging the at least one projection of the first jaw, wherein moving the sliding cam relative to the second jaw moves the first jaw relative to the second jaw from an open condition for receiving the first fixation element between the jaws to a clamping condition for capturing the first fixation element between the jaws; and
a second clamp comprising jaws moveable relative to one another between an open condition arranged to receive a second fixation element and a provisionally locked condition arranged to capture the second fixation element.

22. The clamping assembly of claim 21, further comprising a latch selectively disposed between the first and second jaws, the latch being moveable relative to the first and second jaws to position a wedge portion of the latch between respective portions of the first and the second jaws to physically limit the range the first jaw can travel relative to the second jaw to secure the first and second jaws in the provisionally locked condition.

23. The clamping assembly of claim 21, wherein the guide cam slot includes an arcuate portion and a linear portion.

24. The clamping assembly of claim 21, wherein the second jaw comprises wall portions, the first jaw being disposed between the wall portions, the sliding cam being slidably attached to the wall portions.

25. The clamping assembly of claim 24, wherein the wall portions comprise slots formed therein, the slots being disposed to guide movement of the first jaw.

26. The clamping assembly of claim 21, wherein the first and second jaws comprise respective forward and aft ends, the respective forward ends of the first and second jaws being configured to receive the first fixation element, and the sliding cam being configured to slide between the respective forward and aft ends of the first and second jaws.

27. The clamping assembly of claim 1, wherein the first and second jaws comprise respective forward and aft ends, the respective forward ends of the first and second jaws being configured to receive the fixation element, and the sliding cam being configured to slide between the respective forward and aft ends of the first and second jaws.

* * * * *